(12) United States Patent
Hodac et al.

(10) Patent No.: US 6,431,015 B1
(45) Date of Patent: Aug. 13, 2002

(54) DELIVERY APPARATUS WITH INTERCHANGEABLE PIPETTE TIP

(75) Inventors: Agathe Hodac, Rapperswil; Stefano Fornito, Gossau; Werner Hälg, Mannedorf; Nikolaus Ingenhoven, Zurich; Mario Benedetti, Pfäffikon, all of (CH)

(73) Assignee: Tecan Trading AG, Männedorf (CH)

( * ) Notice: Subject to any disclaimer, the term of this patent is extended or adjusted under 35 U.S.C. 154(b) by 0 days.

(21) Appl. No.: 09/691,089

(22) Filed: Oct. 18, 2000

(30) Foreign Application Priority Data

Oct. 21, 1999 (EP) .............................................. 99810957

(51) Int. Cl.$^7$ .................................................. B01L 3/02
(52) U.S. Cl. .................................. 73/864.01; 73/864.11; 73/864.14; 422/100
(58) Field of Search .......................... 73/864.01, 864.11, 73/864.14; 422/100; 264/442

(56) References Cited

U.S. PATENT DOCUMENTS

| 4,444,062 A | * | 4/1984 | Bennet et al. ........... 73/863.32 |
| 5,343,909 A | * | 9/1994 | Goodman ................... 141/242 |
| 5,763,278 A |   | 6/1998 | Sickinger et al. |
| 6,045,757 A | * | 4/2000 | Moriarty et al. ............ 422/100 |
| 6,098,802 A | * | 8/2000 | Asa et al. .................... 206/443 |

FOREIGN PATENT DOCUMENTS

| EP | 0 187 167 | 7/1986 |
| WO | WO 90/14162 | 11/1990 |
| WO | WO 95/00392 | 1/1995 |

* cited by examiner

Primary Examiner—Hezron Williams
Assistant Examiner—C D Garber
(74) Attorney, Agent, or Firm—Notaro & Michalos PC

(57) ABSTRACT

A delivery apparatus has, in a housing (13), a cannula (8) whose rear end is connected to a diluter (17) via a connecting tube (16). A piezoelectric actuator (10) increases in length under the action of a control signal and acts on a membrane (6) pierced by the cannula tip (9) and belonging to an interchangeable polypropylene pipette tip mounted on the delivery apparatus and adhering to the housing (13) by means of a collar (7) resting against said housing, and causing said membrane to sag, with the result that a drop of a sample liquid which was previously sucked in by means of the diluter (17) and whose accurately adjustable volume is between 1 nl and 1 µl is ejected from an outlet orifice (4). After a pipetting process the pipette tip is ejected by means of a slide (15). If the level of the sample liquid in the pipette tip always remains below the cannula tip (9), virtually no carry-over occurs.

19 Claims, 3 Drawing Sheets

DELIVERY APPARATUS WITH INTERCHANGEABLE PIPETTE TIP

FIELD OF THE INVENTION

The invention relates to an interchangeable pipette tip and a method for its production, a delivery apparatus for use with such pipette tips and a pipetting system. Such parts and devices are used in particular in chemical, biological and medical laboratories for pipetting liquids.

PRIOR ART

The Genesis system from TECAN AG comprises a pipetting system which can be operated with interchangeable plastics pipette tips of the generic type, in which the inlet orifice at the rear end is open. Every pipette tip is connected to a diluter by means of a tube which can be led through a solenoid valve. The delivery of a small amount of liquid from the air is then triggered in each case by operating the solenoid valve. The system permits the delivery of liquid amounts between 1 µl and 10 µl with generally sufficient accuracy.

If, however, even smaller amounts of liquid—between 1 nl and 1 µl—are to be delivered with high accuracy, the system described does not meet the requirements in every case.

SUMMARY OF THE INVENTION

It is the object of the invention to provide an interchangeable pipette tip, a delivery apparatus for use with such pipette tips and a pipetting system, which permit the delivery of very small amounts of liquid—in particular in the range from 1 nl to 1 µl—with high accuracy. In addition, it is intended to provide a suitable method for the production of an interchangeable pipette tip. This object is achieved by the invention as characterized in the Claims.

The advantages achieved by the invention are in particular that even very small volumes of liquid can be delivered with high accuracy. Moreover, carry-over of sample liquid between successive pipetting operations and its possible consequences, such as falsification of results or clogging of lines by agglomeration, are kept at an extremely low level, since the pipette tips can in each case be changed in between and direct contact of other parts of the delivery apparatus with the sample liquid can be avoided. The pipette tips can be produced very economically so that frequent changing thereof is scarcely an important factor with regard to the costs. The delivery apparatus, too, is relatively cheap to produce.

BRIEF DESCRIPTION OF THE DRAWINGS

Below, the invention is explained in more detail with reference to Figures, which represent only an embodiment.

DESCRIPTION OF THE PREFERRED EMBODIMENTS

Figure 1:
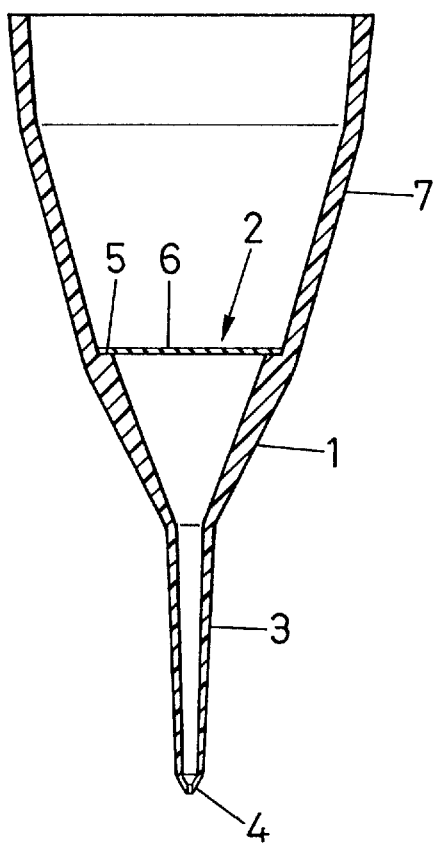
FIG. 1 shows a longitudinal section through an interchangeable pipette tip according to the invention.

The interchangeable pipette tip according to the invention is (FIG. 1) rotationally symmetrical and comprises a relatively rigid all-round wall which comprises a wider container 1 which, starting from an inlet orifice 2, tapers in a funnel-like manner and becomes a narrower outflow tube 3, at the end of which an outlet orifice 4 is arranged. The wall forms an all-round ledge 5 which surrounds the inlet orifice 2 and to which the edge of a flexible membrane 6 is connected, which membrane hermetically seals the inlet orifice 2. Above the ledge 5, the wall forms a widening all-round collar 7.

The volume of the cavity enclosed by the container 1, the outflow 3 and the membrane 6 is as a rule between 10 µl and 200 µl. The diameter of the outlet orifice is between about 50 µm and 100 µm. The membrane has a thickness of between 200 µm and 500 µm, depending on diameter and desired deflectability and, as a rule, the thickness is not greater than 300 µm and is preferably about 250 µm.

The interchangeable pipette tip is preferably produced in such a way that the all-round wall—without outlet orifice—is produced by the injection moulding method and is provided with the outlet orifice 4 by laser drilling. The membrane 6 is then mounted by, for example, ultrasonically welding its edge to the ledge 5. The pipette tip may consist of polypropylene. As an alternative to the method described, the wall can be produced with a larger outlet orifice by the injection moulding method and said orifice can then be narrowed to the desired diameter by heating and drawing of the outflow tube 3.

The production methods described are simple and can be readily automated, so that the price of the pipette tip intended as a disposable tip for a single use can be kept very low.

Figure 2:
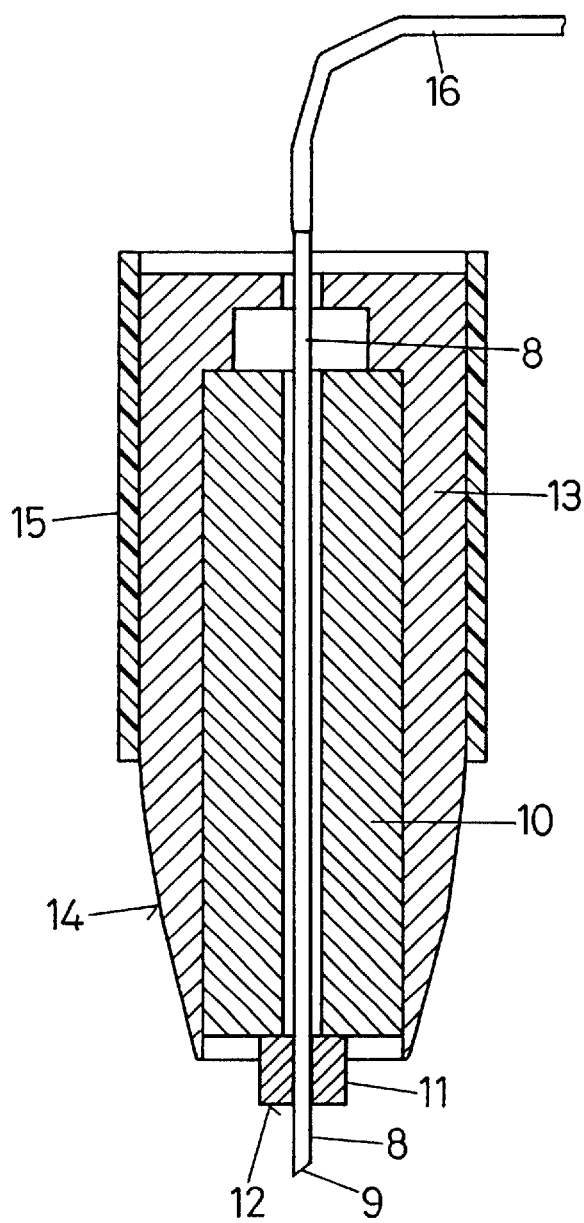
FIG. 2 shows a longitudinal section through a delivery apparatus according to the invention, FIG. 3 schematically shows a pipetting system according to the invention, comprising a delivery apparatus with mounted interchangeable pipette tip.

The delivery apparatus according to the invention (FIG. 2) comprises a cannula 8 having an internal diameter 0.5 mm or less, which is cut obliquely at the front end and forms a cannula tip 9, when it has a constriction in the vicinity of its rear end. The cannula 8 is surrounded by a tubular actuator 10 which is in the form of a stack of piezoelectric elements and whose length can be temporarily increased by between 5 µm and 15 µm by an electrical signal. A transfer piece 11 which is fastened to the cannula 8 and is joined to the end of the actuator 10 and surrounds the cannula 8 in an annular manner is connected in the region of the cannula tip 9. Said transfer piece forms an abutting surface 12 which is slightly recessed relative to the cannula tip 9, surrounds the cannula 8 in an annular manner and can be pushed forwards and pulled back by means of the actuator 10 together with the cannula 8, parallel to the axis thereof.

The cannula 8 and the actuator 10 are anchored in a brass or steel housing 13 which surrounds them and forms an outward-facing all-round contact surface 14 which widens with increasing distance from an edge located at about the height of the transfer piece 11. Adjacent to the contact surface 14, the housing 13 is surrounded by a tubular slide 15 which can be pushed forward over the contact surface 14 and drawn back from it, for example by means of an electric drive. The rear end of the cannula 8 projects slightly beyond the housing 13 so that a connecting tube 16 can be connected here. The delivery apparatus is essentially rotationally symmetrical.

Figure 3:
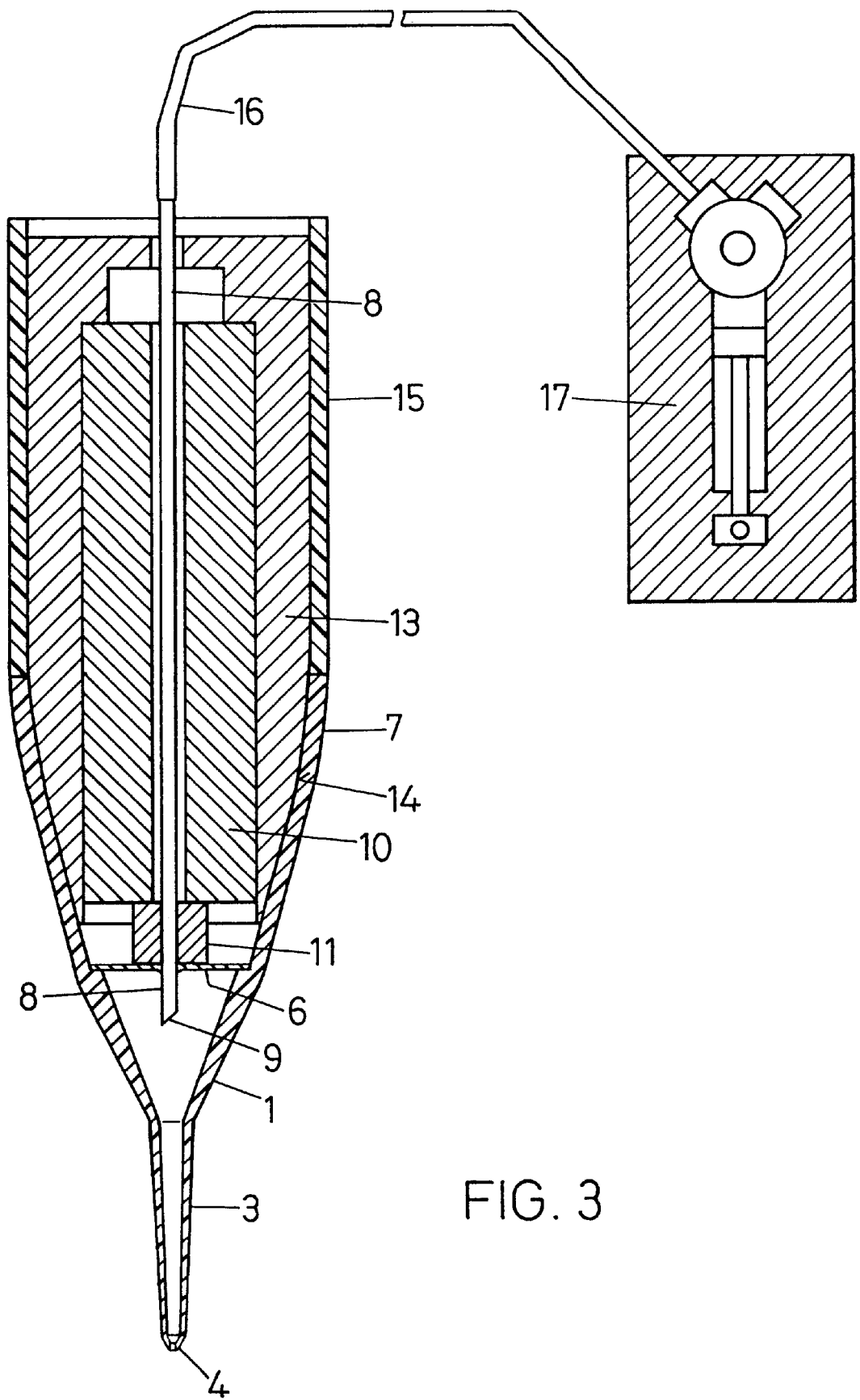

The pipetting system shown in FIG. 3 comprises a delivery apparatus as described above and a diluter 17 which is connected by the connecting tube 16 to the rear end of the cannula 8. Instead of a diluter, it is also possible to provide another suction pump or pressure and suction pump. In practice, a pipetting system usually comprises a plurality of delivery apparatuses which are each connected to a diluter and together fastened to a robot arm, for example one which can be moved along three axes. A rack containing new pipette tips and a waste container or rack for holding spent pipette tips are then also arranged in the region of the robot arm.

Figure 4:
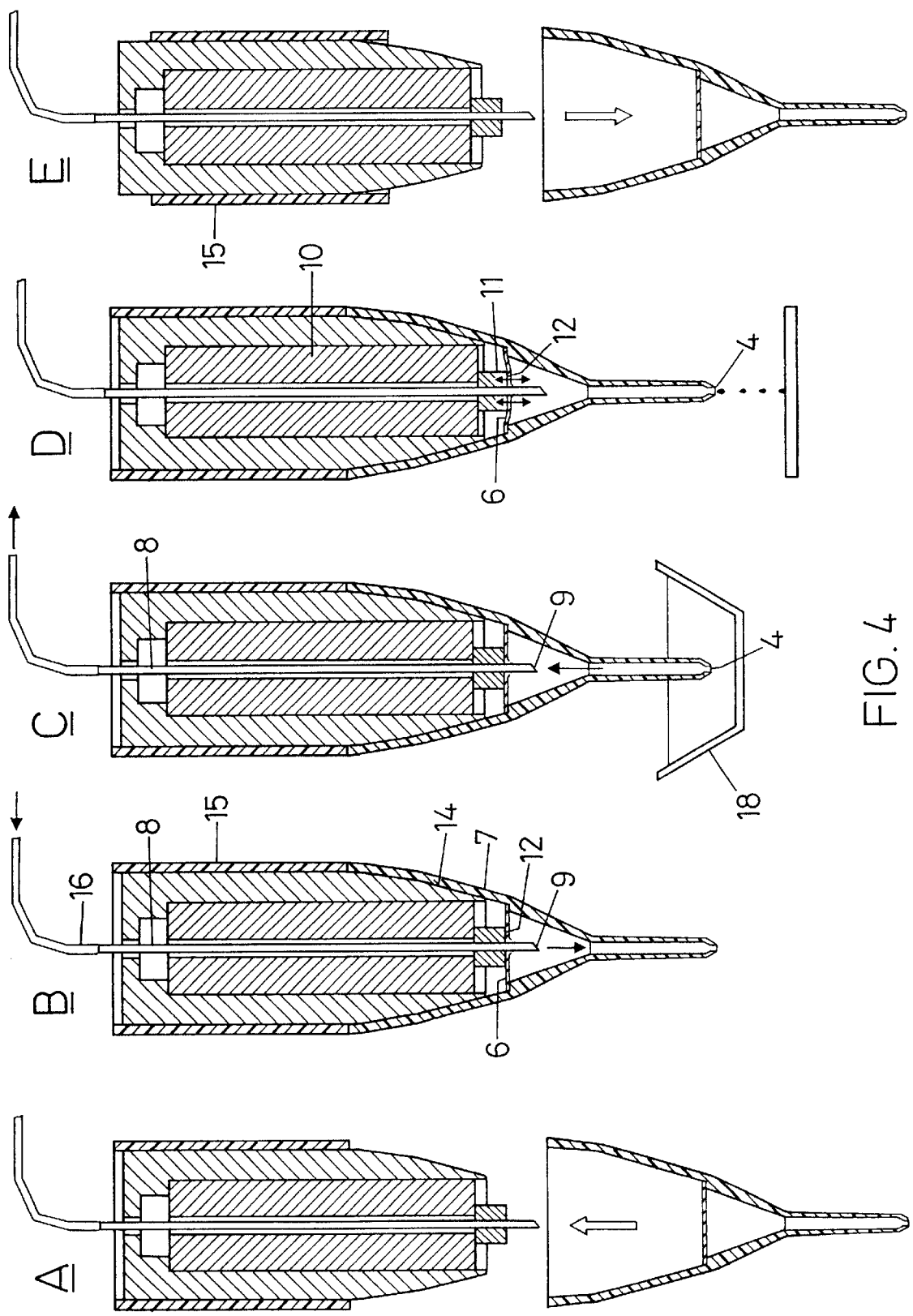
FIG. 4 shows a delivery apparatus and interchangeable pipette tip according to the invention in longitudinal section during various stages of a pipetting process.

The pipetting of liquid samples can now take place as shown in FIG. 4. First, the delivery apparatus is guided to a rack containing new interchangeable pipette tips and a pipette tip is picked up by bringing (A) the delivery apparatus above said pipette tip and then lowering said apparatus until the cannula tip 9 pierces the membrane 6 and the abutting surface 12 rests against the upper surface of said membrane. The collar 7 is slightly elastically expanded by the contact surface 14. The inner surface of said collar rests firmly against said contact surface so that the pipette tip fits reliably on the delivery apparatus. The edge of the collar 7 abuts the lower edge of the slide 15. The pipette tip is then filled by means of the diluter 17 (FIG. 3) via the connecting tube 16 and the cannula 8 with inert system liquid, e.g. distilled water (FIG. 4B).

The delivery apparatus is then brought above a reservoir 18 containing the sample liquid to be pipetted and is lowered until the outlet orifice 4 of the pipette tip is immersed. A sufficient amount of the sample liquid is then sucked into the cavity of the pipette tip, once again by means of the diluter 17 (FIG. 3). Its level should remain below the cannula tip 9 (FIG. 4C) so that there is no direct contact between the cannula 8 and the sample liquid. Contamination of the cannula 8 is then possible only on mixing of the sample liquid with the system liquid, to a very small, usually negligible extent. Carry-over between two successive pipetting operations and its possible consequences, such as falsification of results or clogging of lines due to agglomeration, are virtually completely ruled out.

(D), the dropwise delivery of the sample liquid onto reagents or the like from the air, now follows. For delivery of a drop, the actuator 10 of the delivery apparatus is briefly stretched in each case by means of an electrical pulse, so that the transfer piece 11 with the cannula 8 is advanced. The abutting surface 12 then bends the flexible membrane 6 so that the volume of the cavity in the pipette tip is briefly reduced and a drop of the sample liquid is ejected through the outlet orifice 4. The cavity of the pipette tip thus acts as a pump chamber. The volume of the ejected drop can be controlled by the size and shape of the signal. Owing to the accuracy with which this control is possible and the fact that the action on the system liquid takes place directly at the pipette tip itself, the ejected volume can be very accurately adjusted even in the case of very small amounts—as a rule, the drop volume is between 1 nl and $1\mu l$. It is of course also possible to eject a plurality of drops in succession, in which case the rate of liquid delivery is also influenced by the frequency of the signals.

After the end of the delivery, the delivery apparatus is brought, for example, above a waste container and the pipette tip is ejected by advancing the slide 15 (E). The described process comprising the stages A to E can be repeated as often as desired.

Of course, various deviations from the embodiment described are possible without departing from the scope of the invention. Thus, for example, a magnetic or pneumatic actuator may be provided. The pipette tips can be prefilled with system liquid, in which case stage B of the pipetting process is omitted.

LIST OF REFERENCE SYMBOLS

1 Container
2 Inlet orifice
3 Outflow tube
4 Outlet orifice
5 Ledge
6 Membrane
7 Collar
8 Cannula
9 Cannula tip
10 Actuator
11 Transfer piece
12 Abutting surface
13 Housing
14 Contact surface
15 Slide
16 Connecting tube
17 Diluter
18 Reservoir

What is claimed is:
1. A pipetting system comprising:
an interchangeable pipette tip having a rigid all-round wall surrounding a cavity and interrupted by an outlet orifice, a larger inlet orifice a distance away from the outlet orifice, and a flexible membrane covering the inlet orifice; and
a delivery apparatus for attaching the interchangeable pipette tip comprising:
a cannula having a cannula tip;
an abutting surface arranged slightly recessed in the proximity of the cannula tip; and
an actuator, by means of which the abutting surface can be moved forwards and backwards essentially parallel to an axis of the cannula.
2. The pipetting system according to claim 1, wherein the cannula tip pierces the flexible membrane and the abutting surface rests against the upper surface of the flexible membrane of the pipette tip.
3. The pipetting system according to claim 1, wherein the rigid wall forms a wider container adjacent the inlet orifice, and a narrower outflow tube adjacent the container, the outlet orifice located at the other end of the outflow tube.
4. The pipetting system according to claim 3, wherein the container narrows continuously from the inlet orifice to the start of the outflow tube.
5. The pipetting system according to claim 1, wherein the rigid wall comprises a collar projecting beyond the edge of the inlet orifice.
6. The pipetting system according to claim 1 wherein the delivery apparatus is rotationally symmetrical with respect to an axis passing through the outlet orifice and the inlet orifice.
7. The pipetting system according to claim 1, wherein the volume of the cavity not greater than 200 $\mu l$.
8. The pipetting system according to claim 1, wherein the diameter of the outlet orifice is between 50–100 $\mu m$.
9. The pipetting system according to claim 1, wherein thickness of the membrane is between 200–500 $\mu m$.
10. The pipetting system according to claim 9, wherein the thickness of the membrane is between 200–300 $\mu m$.
11. The pipetting system according to claim 1, wherein the delivery apparatus is made at least in part from polypropylene.

12. The pipetting system according to claim 1, wherein the actuator surrounds the cannula.

13. The pipetting system according to claim 1, wherein the abutting surface forms the front surface of a transfer piece supported on the actuator.

14. The pipetting system according to claim 13, wherein the transfer piece is connected to the cannula.

15. The pipetting system according to claim 1, wherein the actuator contains at least one piezoelectric element.

16. The pipetting system according to claim 1, wherein the delivery apparatus further comprises a housing surrounding the cannula and the actuator, the housing forming an outward-facing contact surface.

17. The pipetting system according to claim 16, further comprising a slide movable forwards and backwards at least over a part of the contact surface.

18. The pipetting system according to claim 1, further comprising a suction pump and a connecting tube connecting the rear end of the cannula to the suction pump.

19. The pipetting system according to claim 18, wherein the suction pump is a diluter.

* * * * *